United States Patent [19]

Gordon

[11] Patent Number: 4,636,522

[45] Date of Patent: Jan. 13, 1987

[54] ACYLAMINOALKANOYL URETHANES OR THIOURETHANES

[75] Inventor: Eric M. Gordon, Pennington, N.J.

[73] Assignee: E. R. Squibb & Sons, Inc., Princeton, N.J.

[21] Appl. No.: 715,217

[22] Filed: Mar. 22, 1985

[51] Int. Cl.$^4$ .................. C07D 207/04; A61K 31/40; A61K 31/34; A61K 31/38
[52] U.S. Cl. .................... 514/423; 562/439; 548/953; 514/333; 514/339; 514/341; 514/343; 514/397; 514/414; 546/147; 546/256; 546/268; 546/273; 546/276; 546/278; 546/281; 548/188; 548/336; 548/356; 548/454; 548/455; 548/456; 548/465; 548/467; 548/468; 548/517; 548/527; 548/533; 560/16; 560/19; 560/24; 560/34; 562/426; 562/433
[58] Field of Search ............... 514/423, 333, 339, 341, 514/343, 397, 414; 548/533, 336, 467, 468, 517, 548/527; 546/256, 273, 276, 278, 281

[56] References Cited

U.S. PATENT DOCUMENTS

| 4,311,705 | 1/1982 | Ondetti et al. .................. 514/423 X |
| 4,329,473 | 5/1982 | Almquist et al. .................. 546/281 |
| 4,470,973 | 9/1984 | Natarajan et al. ............... 546/245 X |
| 4,524,212 | 6/1985 | Gordon et al. .................. 514/423 X |

FOREIGN PATENT DOCUMENTS 17203 1/1984 Australia .

OTHER PUBLICATIONS

Meyer et al., "Novel Synthesis of . . . ", J. Med. Chem., 1981, vol. 24, pp. 964-969.
Almquist et al., "Derivatives of Potent Angiotensin Converting Enzyme Inhibitor . . . ", J. Med. Chem, 1982, vol. 25, 1292-1299.

*Primary Examiner*—Joseph Paul Brust
*Attorney, Agent, or Firm*—Lawrence S. Levinson; Stephen B. Davis

[57] ABSTRACT

Compounds of the formula

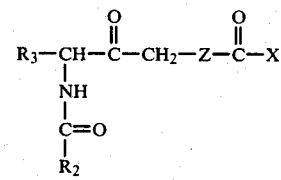

wherein Z is oxygen or sulfur are disclosed. These compounds are useful as hypotensive agents due to their angiotensin converting enzyme inhibition activity and depending upon the definition of X may also be useful as analgesics due to their enkephalinase inhibition activity.

9 Claims, No Drawings

ACYLAMINOALKANOYL URETHANES OR THIOURETHANES

BACKGROUND OF THE INVENTION

Natarajan et al. in Australian Patent Application No. 17,203 disclose acylalkylaminocarbonyl substituted amino and imino acid compounds of the formula

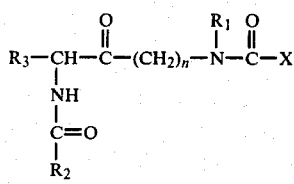

wherein $R_2$ is certain aryl, aralkyl, hetero, or alkylene-hetero groups. These compounds possess angiotensin converting enzyme inhibition activity and enkephalinase inhibition activity depending upon the definition of X.

Almquist et al. in U.S. Pat. No. 4,329,473 disclose angiotensin converting enzyme inhibiting compounds of the formula

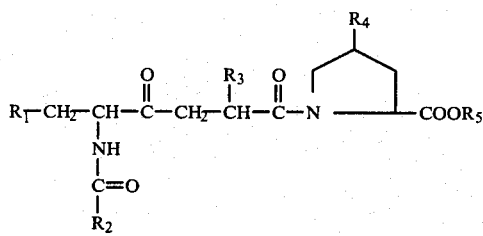

wherein $R_2$ is aryl, alkyl, alkoxy or benzyloxy.

SUMMARY OF THE INVENTION

This invention is directed to novel compounds of the formula

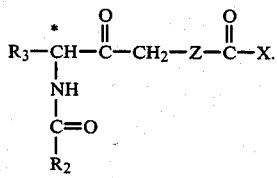  (I)

Z is oxygen or sulfur.

X is an amino or imino acid or ester of the formula

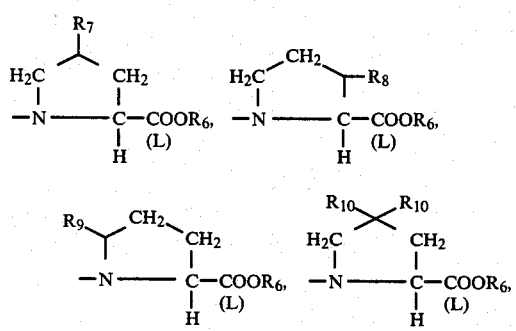

-continued

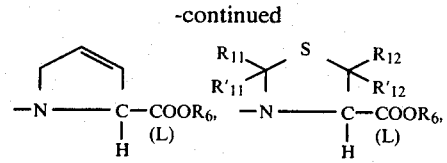

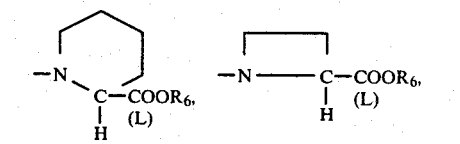

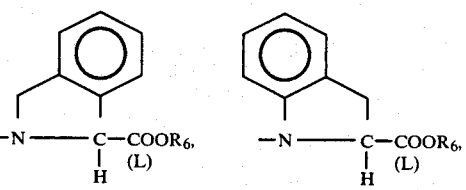

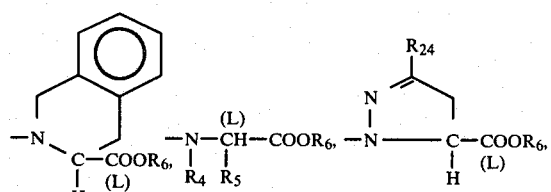

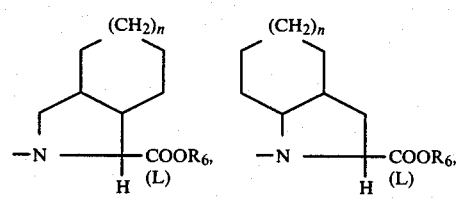

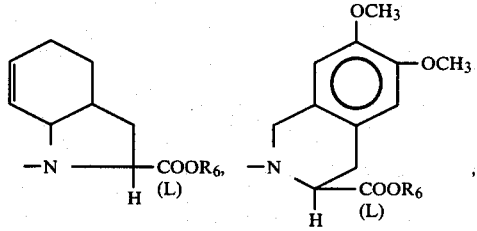

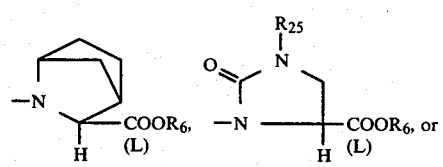

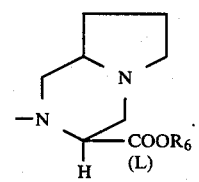

n is zero, one or two.

$R_{25}$ is lower alkyl of 1 to 4 carbons or

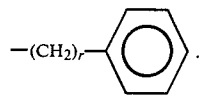

$R_7$ is hydrogen, lower alkyl, halogen, hydroxy,

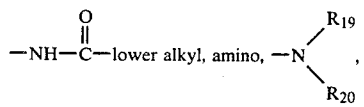

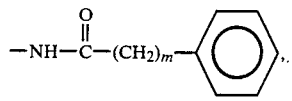

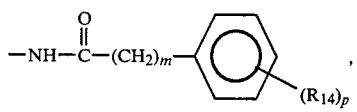

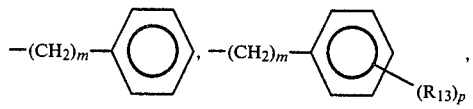

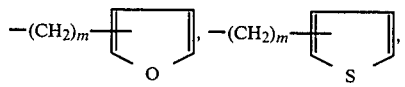

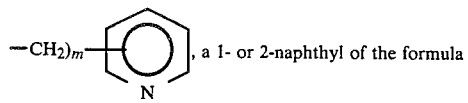, a 1- or 2-naphthyl of the formula

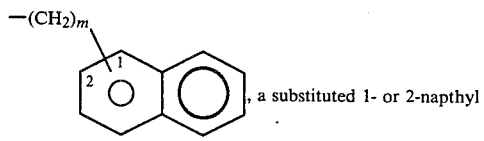, a substituted 1- or 2-napthyl of the formula 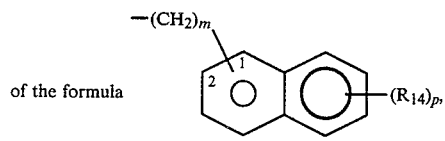,

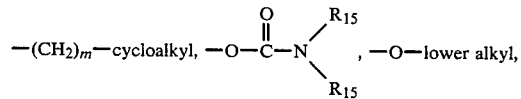

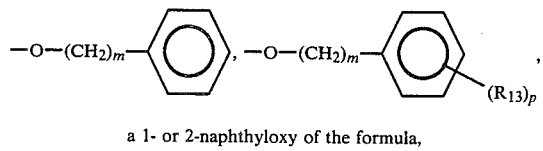

a 1- or 2-naphthyloxy of the formula,

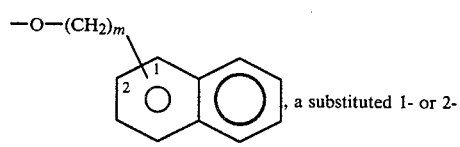, a substituted 1- or 2- naphthyloxy of the formula

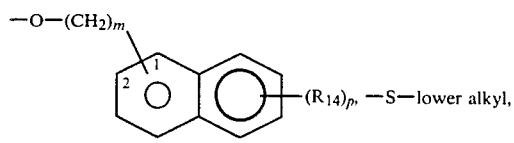

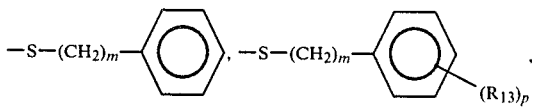

a 1- or 2-naphthylthio of the formula

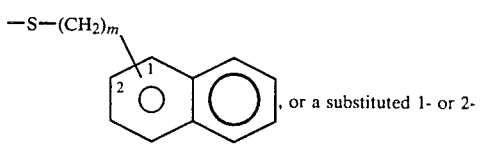, or a substituted 1- or 2- naphthylthio of the formula

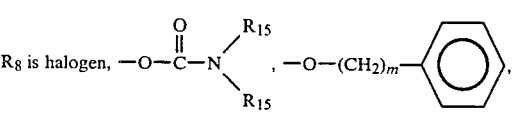

$R_8$ is halogen, 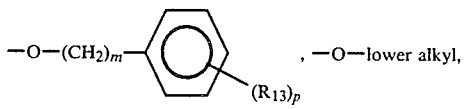

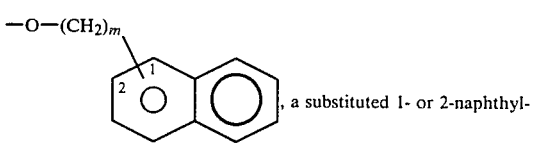, —O—lower alkyl, a 1- or 2-naphthyloxy of the formula

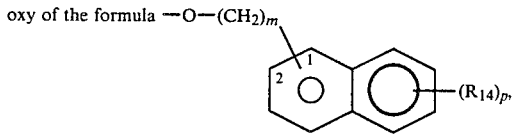, a substituted 1- or 2-naphthyloxy of the formula —O—(CH$_2$)$_m$

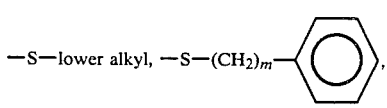

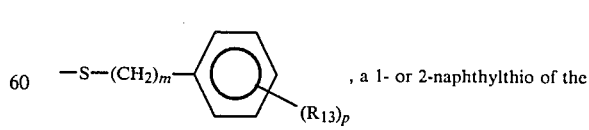, a 1- or 2-naphthylthio of the formula 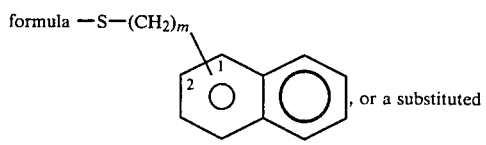, or a substituted

-continued
1- or 2-naphthylthio of the formula

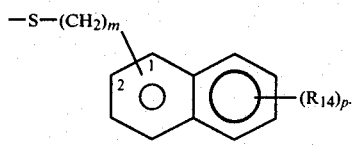

$R_9$ is keto, $-(CH_2)_m-\phi$, or

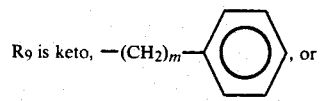

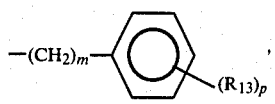

$R_{10}$ is halogen or $-Y-R_{16}$.
$R_{11}$, $R'_{11}$, $R_{12}$ and $R'_{12}$ are independently selected from hydrogen and lower alkyl or $R'_{11}$, $R_{12}$ and $R'_{12}$ are hydrogen and $R_{11}$ is

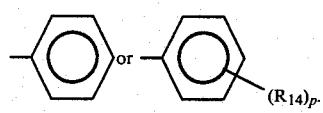

$R_{13}$ is lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl.
$R_{14}$ is lower alkyl of 1 to 4 carbons, lower alkoxy of 1 to 4 carbons, lower alkylthio of 1 to 4 carbons, chloro, bromo, fluoro, trifluoromethyl or hydroxy.
m is zero, one, two, three, or four.
p is one, two or three provided that p is more than one only if $R_{13}$ or $R_{14}$ is methyl, methoxy, chloro, or fluoro.
$R_{15}$ is hydrogen or lower alkyl of 1 to 4 carbons.
Y is oxygen or sulfur.
$R_{16}$ is lower alkyl of 1 to 4 carbons,

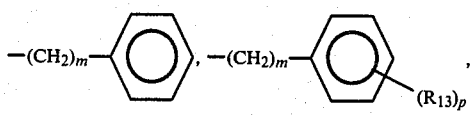

or the $R_{16}$ groups join to complete an unsubstitued 5- or 6-membered ring or said ring in which one or more of the carbons has a lower alkyl of 1 to 4 carbons or a di(lower alkyl of 1 or 4 carbons) substituent.

$R_4$ is hydrogen, lower alkyl,

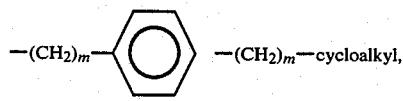

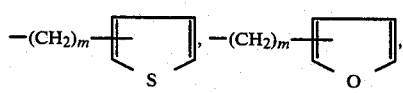

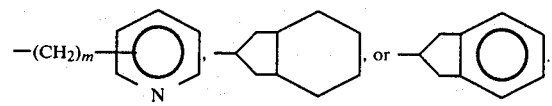

$R_5$ is hydrogen, lower alkyl, $-(CH_2)_r-\phi$,

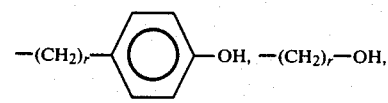

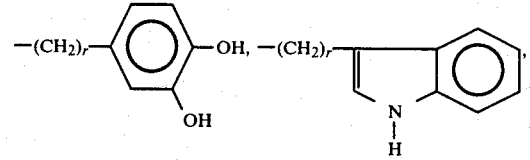

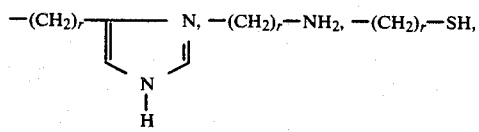

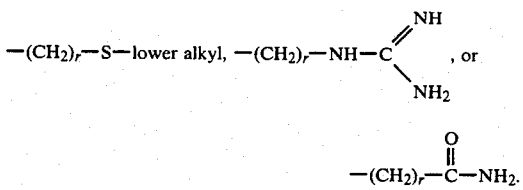

$-(CH_2)_r-\overset{O}{\overset{\|}{C}}-NH_2$.

r is an integer form 1 to 4
$R_{19}$ is lower alkyl, benzyl or phenethyl.
$R_{20}$ is hydrogen, lower alkyl, benzyl or phenethyl.

$R_3$ is hydrogen, lower alkyl,

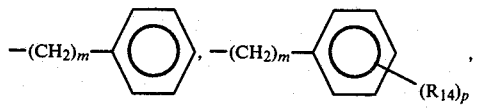

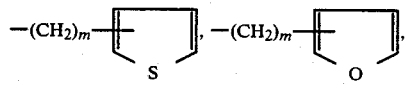

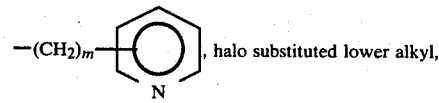

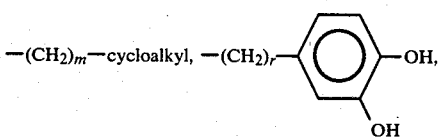

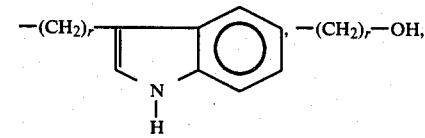

-continued

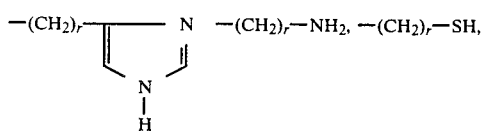

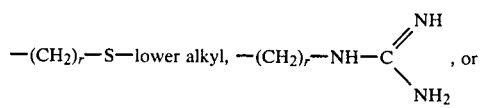

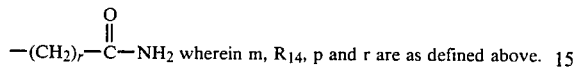

wherein m, $R_{14}$, p and r are as defined above.

$R_2$ is 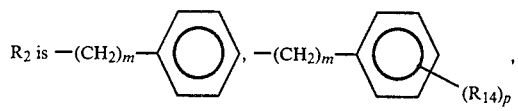

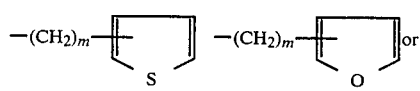 or

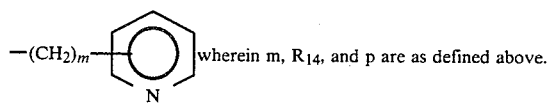 wherein m, $R_{14}$, and p are as defined above.

$R_6$ is hydrogen, lower alkyl, benzyl, benzhydryl,

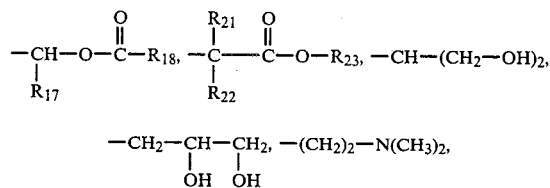

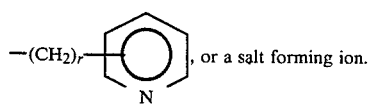

$R_{17}$ is hydrogen, lower alkyl, cycloalkyl, or phenyl.
$R_{18}$ is hydrogen, lower alkyl, lower alkoxy or phenyl.
$R_{21}$ and $R_{22}$ are independently selected from hydrogen and lower alkyl.
$R_{23}$ is lower alkyl.
$R_{24}$ is hydrogen, lower alkyl,

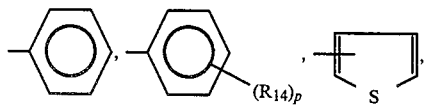

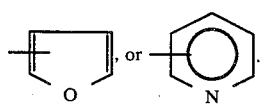

DETAILED DESCRIPTION OF THE INVENTION

This invention in its broadest aspects relates to the amino and imino acid and ester compounds of formula I and to compositions and the method of using such compounds as pharmaceutical agents.

The term lower alkyl used in defining various symbols refers to straight or branched chain radicals having up to seven carbons. The preferred lower alkyl groups are up to four carbons with methyl and ethyl most preferred. Similarly the terms lower alkoxy and lower alkylthio refer to such lower alkyl groups attached to an oxygen or sulfur.

The term cycloalkyl refers to saturated rings of 4 to 7 carbon atoms with cyclopentyl and cyclohexyl being most preferred.

The term halogen refers to chloro, bromo and fluoro.

The symbols

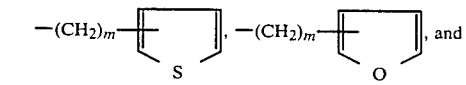

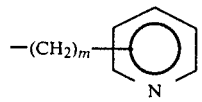

represent that the alkylene bridge is attached to an available carbon atom.

The compounds of formula I are obtained by treating an alcohol or mercaptan of the formula

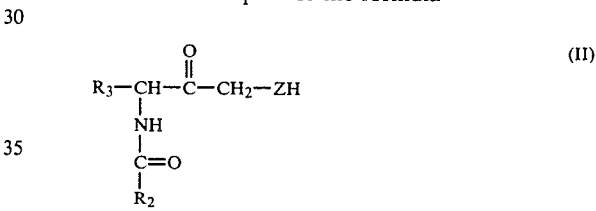 (II)

with phosgene in the presence of N-methylmorpholine and reacting the resulting compound with the amino or imino acid ester of the formula

HX      (III)

particularly the hydrochloride salt thereof, wherein $R_6$ in the definition of X is an easily removably protecting group such as benzyl, benzhydryl, t-butyl, etc.

Alternatively, the amino or imino acid ester of formula III could be first treated with phosgene and that product then reacted with the alcohol or mercaptan of formula II.

Removal of the $R_6$ protecting group, for example, by hydrogenation when $R_6$ is benzyl, yields the acid products of formula I, i.e., $R_6$ is hydrogen.

The alcohol intermediates of formula II, i.e., Z is oxygen, can be prepared by treating a chloroketone of the formula

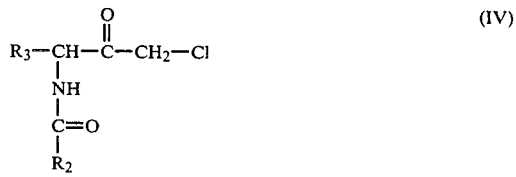 (IV)

with tetrabutylammonium trifluoroacetate in an aqueous acetone solution.

The mercaptan intermediates of formula II, i.e., Z is sulfur, can be prepared by treating the chloroketone of formula IV with sodium thioacetate and then treating the resulting S-acetyl product with ammonia or sodium hydroxide.

The chloroketone of formula IV can be prepared as taught in Australian Patent Application 17,203 by treating a chloroketone of the formula

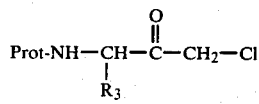 (V)

wherein Prot is a protecting group such as benzyloxycarbonyl, with hydrogen bromide and acetic acid followed by reaction with acid halide of the formula

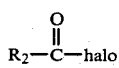 (VI)

wherein halo is Cl or Br in the presence of base such as sodium bicarbonate.

In the above reactions if either $R_3$ or $R_5$ or both are

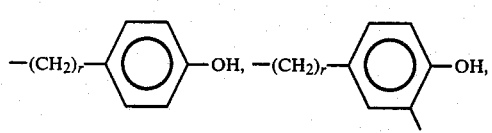

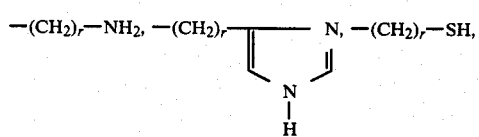

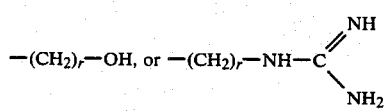

then the hydroxyl, amino, imidazolyl, mercaptan or guanidinyl function should be protected during the reaction. Suitable protecting groups include benzyloxycarbonyl, t-butoxycarbonyl, benzyl, benzhydryl, trityl, etc., and nitro in the case of guanidinyl. The protecting group is removed by hydrogenation, treatment with acid, or other known methods following completion of the reaction.

The ester products of formula I wherein $R_6$ is

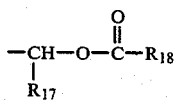

may be obtained by employing the amino or imino acid ester of formula III in the above reactions with such ester group already in place.

The ester products of formula I wherein $R_6$ is

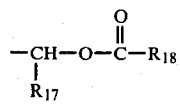

can also be obtained by treating the product of formula I wherein $R_6$ is hydrogen with a molar excess of the compound of the formula

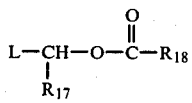 (VII)

wherein L is a leaving group such as chlorine, bromine, tolylsulfonyl, etc.

The ester products of formula I wherein $R_6$

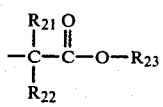

can be prepared by treating the product of formula I wherein $R_6$ is hydrogen with a molar excess of the compound of the formula

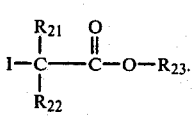 (VIII)

The ester products of formula I wherein $R_6$ is

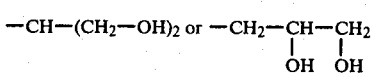

can be prepared by coupling the product of formula I wherein $R_6$ is hydrogen with a molar excess of the compound of the formula

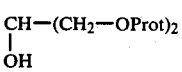 (IX)

or the formula

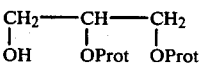 (X)

in the presence of a coupling agent such as dicyclohexylcarbodiimide and the optional presence of a catalyst such as dimethylaminopyridine followed by removal of the hydroxyl protecting group.

Similarly, the ester products of formula I wherein $R_6$ is

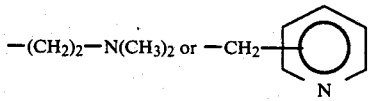

can be prepared by coupling the product of formula I wherein $R_6$ is hydrogen with a molar excess of the compound of formula

    (XI)

or the formula

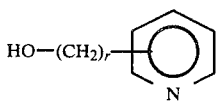    (XII)

in the presence of a coupling agent such as dicyclohexylcarbodiimide and the optional presence of a catalyst such as dimethylaminopyridine.

The products of formula I wherein $R_7$ is amino may be obtained by reducing the corresponding products of formula I wherein $R_7$ is azido.

Preferred compounds of this invention are those of formula I wherein:

X is:

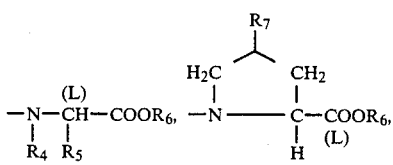

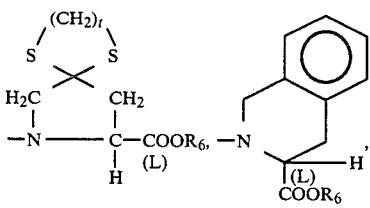

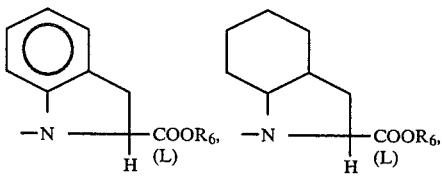

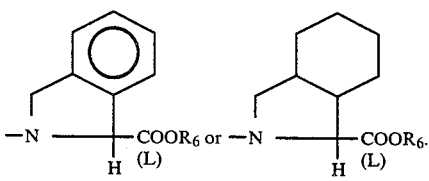

$R_6$ is hydrogen straight or branched chain lower alkyl of 1 to 4 carbons, or an alkali metal salt ion.
$R_4$ is cyclohexyl or phenyl and $R_5$ is hydrogen.
$R_4$ is hydrogen and $R_5$ is methyl,

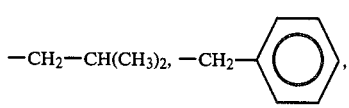

-continued

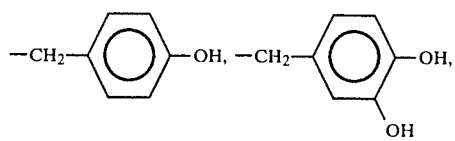

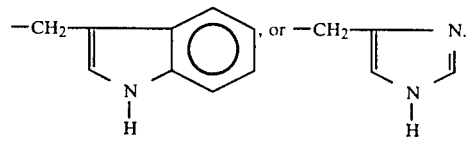

$R_7$ is hydrogen, cyclohexyl, lower alkoxy of 1 to 4 carbons,

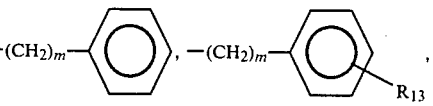

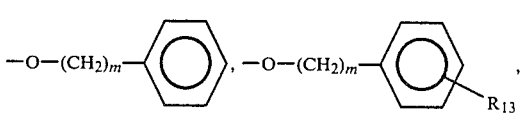

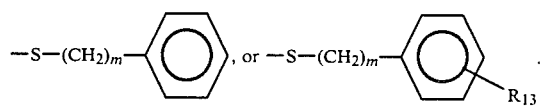

$R_{13}$ is methyl, methoxy, methylthio, Cl, Br, F, or hydroxy.
m is zero, one or two.
t is two or three.
$R_2$ is

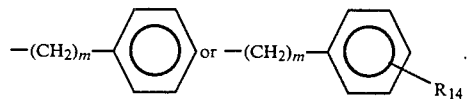

$R_3$ is straight or branched chain lower alkyl of 1 to 4 carbons,

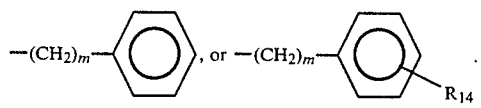

$R_{14}$ is methyl, methoxy, methylthio, Cl, Br, F, or hydroxy.

Most preferred compounds of this invention are those of formula I wherein:

X is

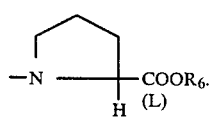

Z is oxygen.
$R_6$ is hydrogen or an alkali metal salt ion.
$R_2$ is phenyl.

R₃ is phenylmethyl.

The compounds of formula I wherein R₆ is hydrogen form salts with a variety of inorganic or organic bases. The nontoxic, pharmaceutically acceptable salts are preferred, although other salts are also useful in isolating or purifying the product. Such pharmaceutically acceptable salts include alkali metal salts such as sodium, potassium or lithium, alkaline earth metal salts such as calcium or magnesium, and salts derived from amino acids such as arginine, lysine, etc. The salts are obtained by reacting the acid form of the compound with an equivalent of the base supplying the desired ion in a medium in which the salt precipitates or in aqueous medium and then lyophilizing.

The compounds of formula I when R₃ is other than hydrogen contain an asymmetric center as represented by the * in formula I. Thus, the compounds of formula I can exist in diastereomeric forms or in mixtures thereof. The above described processes can utilize racemates, enantiomers or diastereomers as starting materials. When diastereomeric products are prepared, they can be separated by conventional chromatographic or fractional crystallization methods.

The products of formula I wherein the imino acid ring is monosubstituted give rise to cis-trans isomerism. The configuration of the final product will depend upon the configuration of the R₇, R₈ and R₉ substituent in the starting material of formula III.

The compounds of formula I, and the pharmaceutically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg., preferably about 1 to 50 mg., per kg. of body weight per day is appropriate to reduce blood pressure. The substance is preferably administered orally but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 330 mg. of a compound of this invention, and about 15 to 300 mg., preferably about 15 to 200 mg. of the diuretic, to a mammalian species in need thereof. Exemplary of the diuretics contemplated for use in combination of this invention are the thiazide diuretics, e.g., chlorothiazide, hydrochlorothiazide, flumethiazide, hydroflumethiazide, bendroflumethiazide, methyclothiazide, trichloromethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of formula I wherein X is

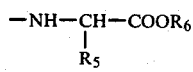

also possess enkephalinase inhibition activity and are useful as analgesic agents. Thus, by the administration of a composition containing one or a combination of such compounds of formula I or a pharmaceutically acceptable salt thereof, pain is alleviated in the mammalian host. A single dose, or preferably two to four divided daily doses, provided on a basis of about 0.1 to about 100mg. per kilogram of body weight per day, preferably about 1 to about 50 mg. per kilogram per day, produces the desired analgesic activity. The composition is preferably administered orally but parenteral routes such as subcutaneous can also be employed.

The following examples are illustrative of the invention. Temperatures are given in degrees centigrade.

EXAMPLE 1

1-[[[(S)-3-(Benzoylamino)-2-oxo-4-phenylbutyl]oxy]-carbonyl]-L-proline (a) (S)-3-Amino-1-chloro-4-phenyl-2-butanone, hydrogen bromide (S)-[3-Chloro-2-oxo-1-(phenylmethyl)propyl]carbamic acid, phenylmethyl ester (51.4 g.) is dissolved in a mixture of acetic acid (252 ml.) and hydrogen bromide in acetic acid (3.45N, 348 ml.) and kept at room temperaure for 1.5 hours. The reaction mixture is then concentrated in vacuo and precipitated with ether to obtain 36.6 g. of (S)-3-amino-1-chloro-4-phenyl-2-butanone, hydrogen bromide; m.p. (175°) 177°–179°.

(b) (S)-N-[3-Chloro-2-oxo-1-(phenylmethyl)propyl]-benzamide (S)-3-Amino-1-chloro-4-phenyl-2-butanone, hydrogen bromide (36.3 g., 130.3 mmole) is suspended in 520 ml. of dry tetrahydrofuran and 18.2 ml. of triethylamine (130.3 mmole) with stirring for ten minutes. The mixture is placed in an ice bath and 15.2 ml. of benzoyl chloride is added followed by 10.95 g. of sodium bicarbonate. After 5 minutes the ice bath is removed and the reaction mixture is kept at room temperature for 1.5 hours. The reaction mixture is then concentrated in vacuo and the residue taken up in 1 l. of aqueous methanol (10% water). The precipitate is collected, filtered and washed with methanol to obtain 25.3 g. of (S)-N-[3-chloro-2- oxo-1 -(phenylmethyl)propyl]benzamide;

m.p. (160°) 170°-172° (dec.); $[\alpha]_D^{23} = -129°$ (c=1.7, dimethylformamide).

(c) (S)-N-[3-Hydroxy-2-oxo-1-(phenylmethyl)propyl]-benzamide

Tetrabutylammonium hydroxide (40% by weight, 25 ml) solution in water is triturated with trifluoroacetic acid to a clear end point (phenolphthalein). The solution is concentrated under reduced pressure and the oily residue is chased with toluene (4 times). The residue solidifies upon drying in high vacuum to give 12.0 g. of white solid tetrabutylammonium trifluoroacetate.

A reaction mixture of (S)-N-[3-chloro-2-oxo-1-(phenylmethyl)propyl]benzamide (3.6 g., 11.9 mmole) and tetrabutylammonium trifluoroacetate (8.6 g., 24.0 mmole) in acetone (200 ml., containing 1% water) is refluxed overnight. The reaction mixture is concentrated under reduced pressure and the oily residue is purified by flash chromatography (LPS-1 silica gel; ethyl acetate:hexane, 2:3) to give 1.93 g. of white solid (S)-N-[3-hydroxy-2-oxo-1-(phenylmethyl)propyl] benzamide; m.p. 130°-131°. TLC (silica gel; ethyl acetate:-hexane, 2:3) $R_f = 0.28$.

Anal. calc'd. for $C_{17}H_{17}NO_3$: C, 72.06; H, 6.05; N, 4.94 Found: C, 71.72; H, 6.17; N, 4.79.

(d) 1-[[[(S)-3-(Benzoylamino)-2-oxo-4-phenylbutyl]ox-y]carbonyl]-L-proline, phenylmethyl ester A 12.5% solution of phosgene in benzene (6.4 ml., 6.0 mmole) is added with stirring to a solution of (S)-N-[3-hydroxy-2-oxo-1-(phenylmethyl)propyl]benzamide (1.38 g., 4.87 mmole) in methylene chloride (30 ml., distilled) and N-methylmorpholine (0.80 ml., 7.3 mmole) at −20°. After stirring at −20 ° under nitrogen for 30 minutes and at room temperature for 45 minutes, the reaction mixture is concentrated under reduced pressure and the residue is chased once with methylene chloride (10 ml.). The residue is suspended in methylene chloride (30 ml.) and treated with a solution of L-proline, phenylmethyl ester, hydrochloride (1.78 g., 7.3 mmole) and N-methylmorpholine (1.33 ml., 12.17 mmole) in methylene chloride (30 ml.). After stirring at room temperature overnight, the reaction mixture is concentrated under reduced pressure, the residue is redissolved in ethyl acetate (100 ml.) and washed with water (twice), saturated sodium bicarbonate (twice), 10% potassium bisulfate (twice), dried ($Na_2SO_4$), and concentrated into 2.1 g. of an oily residue. Flash chromatography (LPS-1 silica gel, 30% ethyl acetate/hexane) gives 1.39 g. of 1-[[[(S)-3-(benzoylamino)-2-oxo-4-phenylbutyl]oxy]carbonyl]-L-proline, phenylmethyl ester as a colorless foam. TLC (silica gel, 50% ethyl acetate/hexane) $R_f = 0.3$.

(e) 1-[[[(S)-3-(Benzoylamino)-2-oxo-4-phenylbutyl]ox-y]carbonyl]-L-proline

A solution of the phenylmethyl ester product from part (d) (0.7 g., 1.43 mmole) in ethyl acetate (30 ml.) containing 10% palladium on carbon catalyst (150 mg.) is hydrogenated for 27 hours. The mixture is filtered, the filtrate is quickly extracted with cold 1N sodium hydroxide (2×20 ml.), the aqueous portion is acidified with 10% potassium bisulfate and extracted with ethyl acetate (3 times). The combined ethyl acetate extracts are dried ($Na_2SO_4$) and concentrated under reduced pressure to yield 0.51 g. of 1-[[[(S)-3-(benzoylamino)-2-oxo-4-phenylbutyl]oxy]carbonyl]-L-proline as a white foam; m.p. 55°-65° (glass). $[\alpha]_D^{25} = -33.8°$; (c=0.5, methanol). TLC (silica gel; chloroform:methanol:acetic acid, 18:1:1) $R_f = 0.46$.

Anal. calc'd. for $C_{22}H_{24}N_2O_6 \cdot 1H_2O$: C, 62.43; H, 5.92; N, 6.33 Found: C, 62.49; H, 5.84; N, 5.89.

EXAMPLES 2-27

Following the procedure of Example 1, the alcohol or mercaptan shown in Col. I is treated with phosgene and the resulting product is reacted with the amino or imino acid ester shown in Col. II to give the ester product shown in Col. III. Removal of the $R_6$ ester group yields the corresponding products in acid form, i.e., $R_6$ is hydrogen.

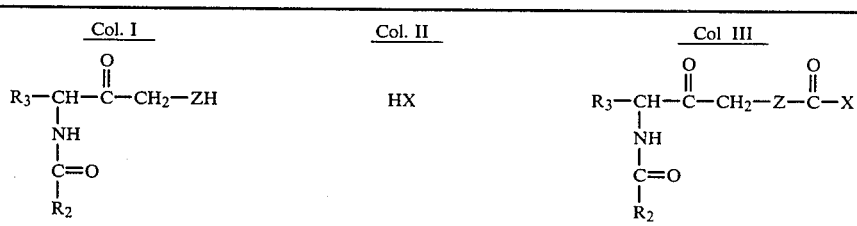

-continued
| | Col. I<br>$R_3-CH-\overset{O}{\overset{\|}{C}}-CH_2-ZH$<br>$\quad\|$<br>$\quad NH$<br>$\quad\|$<br>$\quad C=O$<br>$\quad\|$<br>$\quad R_2$ | Col. II<br>HX | Col III<br>$R_3-CH-\overset{O}{\overset{\|}{C}}-CH_2-Z-\overset{O}{\overset{\|}{C}}-X$<br>$\quad\|$<br>$\quad NH$<br>$\quad\|$<br>$\quad C=O$<br>$\quad\|$<br>$\quad R_2$ | |
|---|---|---|---|---|
| Example | $R_3$ | $R_2$ | Z | X |
| 4 | 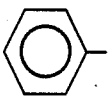 | 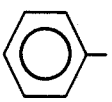 | O |  |
| 5 | 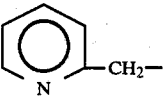 | 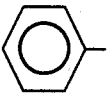 | S | 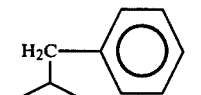 |
| 6 | 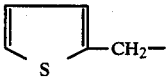 |  | O | 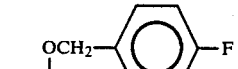 |
| 7 | 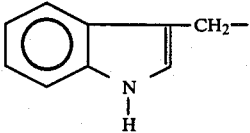 | 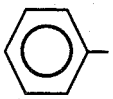 | O | 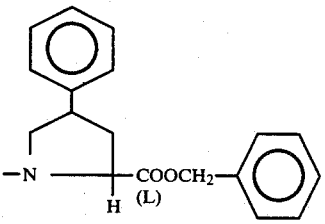 |
| 8 |  |  | S | 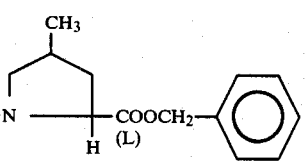 |
| 9 | 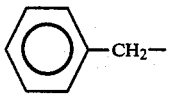 | 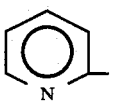 | O | 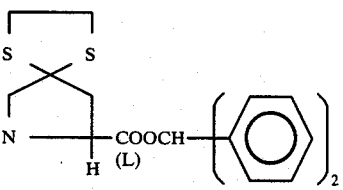 |
| 10 | 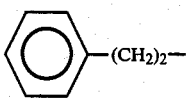 | 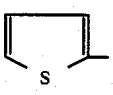 | O | 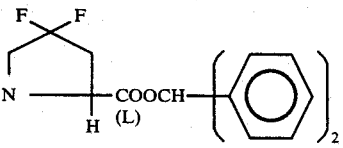 |

-continued

| | Col. I $R_3-CH(NHC(=O)R_2)-C(=O)-CH_2-ZH$ | Col. II HX | Col III $R_3-CH(NHC(=O)R_2)-C(=O)-CH_2-Z-C(=O)-X$ | |
|---|---|---|---|---|
| Example | R₃ | R₂ | Z | X |
| 11 | C₆H₅–CH₂– | 4-CH₃–C₆H₄– | S | –N(L)–CH(CH₂C₆H₄–)(COOCH₂C₆H₅), fused benzyl ring (H) |
| 12 | H₅C₂–H₂C– | C₆H₅– | O | –N–CH(H)(COOCH₂C₆H₅)(L), with o-benzyl linkage |
| 13 | cyclohexyl–CH₂– | C₆H₅– | S | –N–CH(H)(COOCH₂C₆H₅)(L), with o-benzyl linkage |
| 14 | O₂N–HN–C(=NH)–NH–(CH₂)₃– | C₆H₅– | O | –N–CH(H)(COOCH₂C₆H₅)(L), cyclohexyl-fused |
| 15 | C₆H₅–H₂C–O–C₆H₄–CH₂– | C₆H₅– | S | –N–CH(H)(COOC(CH₃)₃)(L), cyclohexyl-fused |
| 16 | C₆H₅–H₂C–O–C(=O)–HN–(CH₂)₄– | C₆H₅– | O | –N–CH(H)(COOCH₂C₆H₅)(L), thiazolidine ring (S) |
| 17 | C₆H₅–H₂C–O–CH₂– | C₆H₅– | O | –N–CH(H)(COOCH₂C₆H₅)(L), cyclopentyl-fused |

-continued

| | Col. I $R_3-CH(NH-C(=O)-R_2)-C(=O)-CH_2-ZH$ | Col. II HX | Col III $R_3-CH(NH-C(=O)-R_2)-C(=O)-CH_2-Z-C(=O)-X$ | |
|---|---|---|---|---|
| Example | R₃ | R₂ | Z | X |
| 18 | Ph-(CH₂)₄- | Ph- | S | -N=N-... CH₃ group with N-N-CH(COOCH(Ph)₂)- |
| 19 | Ph-CH₂- | Ph- | O | -N(Ph)-CH₂-COOCH₂-Ph |
| 20 | Ph-CH₂- | Ph- | S | -N(C₆H₁₁)-CH₂-COOCH(Ph)₂ |
| 21 | (2-pyridyl)-CH₂- | Ph- | O | -NH-CH(L)(CH₃)-COOCH₂-Ph |
| 22 | Ph-CH₂- | (pyridyl)- | S | -NH-CH(L)(CH₂-CH(CH₃)₂)-COOCH(Ph)₂ |
| 23 | Ph-CH₂- | Ph- | O | -NH-CH(L)(CH₂-Ph)-COOCH₂-Ph |
| 24 | Ph-CH₂- | Ph- | O | -NH-CH(L)(CH₂-imidazolyl-N-CH₂-Ph)-COOCH₂-Ph |

-continued

| | Col. I | Col. II | Col III |
|---|---|---|---|
| | $R_3-\underset{\underset{\underset{R_2}{C=O}}{NH}}{CH}-\overset{O}{\overset{\|}{C}}-CH_2-ZH$ | HX | $R_3-\underset{\underset{\underset{R_2}{C=O}}{NH}}{CH}-\overset{O}{\overset{\|}{C}}-CH_2-Z-\overset{O}{\overset{\|}{C}}-X$ |
| Example | $R_3$ | $R_2$ | Z  X |

| Example | $R_3$ | $R_2$ | Z | X |
|---|---|---|---|---|
| 25 | C₆H₅-CH₂– | C₆H₅– | O | –N(H)–CH(CH₂SC₆H₅)–CH₂–COCHOC(O)–C₂H₅ with cyclohexyl (L) |
| 26 | C₆H₅-CH₂– | C₆H₅– | O | –N(H)–CH(propyl ring)–COCHOC(O)–C₂H₅, CH(CH₃)₂ (L) |
| 27 | C₆H₅-CH₂– | C₆H₅– | O | –N(H)–CH(CH₂-cyclohexyl)–COCHOC(O)–C₂H₅, CH(CH₃)₂ |

The $R_3$ protecting groups shown in Examples 14 to 17 and the $R_5$ protecting group shown in Example 24 are removed as the last step in the synthesis. The $R_6$ ester groups shown in Examples 25 to 27 are not removed.

EXAMPLE 28

1000 tablets each containing the following ingredients:

| | |
|---|---|
| 1-[[[(S)—3-(Benzoylamino)-2-oxo-4-phenylbutyl]oxy]carbonyl]-L-proline | 100 mg. |
| Cornstarch | 50 mg. |
| Gelatin | 7.5 mg. |
| Avicel(microcrystalline cellulose) | 25 mg. |
| Magnesium stearate | 2.5 mg. |
| | 185 mg. | are prepared from sufficient bulk quantities by mixing 1-[[[(S)-3-(benzoylamino)-2-oxo-4-phenylbutyl]oxy]carbonyl]-L-proline and cornstarch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

In a similar manner, tablets containing 100 mg. of the product of any of Examples 2 to 27 can be prepared.

A similar procedure can be employed to form tablets containing 50 mg. of active ingredient.

EXAMPLE 29

Two piece #1 gelatin capsules are filled with a mixture of the following ingredients:

| | |
|---|---|
| 1-[[[(S)—3-(Benzoylamino)-2-oxo-4-phenylbutyl]oxy]carbonyl]-L-proline | 50 mg. |
| Magnesium stearate | 7 mg. |
| Lactose | 193 mg. |
| | 250 mg. |

In a similar manner capsules containing 50 mg. of the product of any of Examples 2 to 27 can be prepared.

EXAMPLE 30

An injectable solution is prepared as follows:

| | |
|---|---|
| 1-[[[(S)—3-(Benzoylamino)-2-oxo-4-phenylbutyl]oxy]carbonyl]-L-proline | 500 g. |
| Methyl paraben | 5 g. |
| Propyl paraben | 1 g. |
| Sodium chloride | 25 g. |
| Water for injection | 5 l |

The active substance, preservatives, and sodium chloride are dissolved in 3 liters of water for injection and then the volume is brought up to 5 liters. The solution is filtered through a sterile filter and aseptically filled into presterilized vials which are closed with presterilized rubber closures. Each vial contains 5 ml. of solution in a concentration of 100 mg. of active ingredient per ml. of solution for injection.

In a similar manner, an injectable solution containing 100 mg. of active ingredient per ml. of solution can be prepared for the product of any of Examples 2 to 27.

EXAMPLE 31

1000 tablets each containing the following ingredients:

| | |
|---|---|
| 1-[[[(S)—3-(Benzoylamino)-2-oxo-4-phenylbutyl]oxy]carbonyl]-L-proline | 100 mg. |
| Avicel | 100 mg. |
| Hydrochlorothiazide | 12.5 mg. |
| Lactose | 113 mg. |
| Cornstarch | 17.5 mg. |
| Stearic acid | 7 mg. | are prepared from sufficient bulk quatities by slugging the 1-[[[(S)-3-(benzoylamino)-2-oxo-4-phenylbutyl]oxy]carbonyl]-L-proline, Avicel, and a portion of the stearic acid. The slugs are ground and passed through a #2 screen, then mixed with the hydrochlorothiazide, lactose, cornstarch, and remainder of the stearic acid. The mixture is compressed into 350 mg. capsule shaped tablets in a tablet press. The tablets are scored for dividing in half.

In similar manner, tablets can be prepared containing 100 mg. of the product of any of Examples 2 to 27.

What is claimed is:

1. A compound of the formula $$R_3-CH-\overset{O}{\underset{||}{C}}-CH_2-Z-\overset{O}{\underset{||}{C}}-X$$
$$\underset{|}{NH}$$
$$\underset{|}{C=O}$$
$$R_2$$

including a pharmaceutically acceptable salt thereof wherein:

Z is oxygen or sulfur;

X is [structures showing pyrrolidine-type rings with $R_7$, $R_8$, $R_9$, $R_{10}$ substituents and —COOR$_6$ (L) groups]

[continued structure with —N—C—COOR$_6$ (L)]

$R_7$ is hydrogen, lower alkyl, halogen, hydroxy, $$-NH-\overset{O}{\underset{||}{C}}-\text{lower alkyl, amino,} -N\overset{R_{19}}{\underset{R_{20}}{\diagdown}},$$

$$-NH-\overset{O}{\underset{||}{C}}-(CH_2)_m-\text{phenyl},$$

$$-NH-\overset{O}{\underset{||}{C}}-(CH_2)_m-\text{phenyl}(R_{14})_p,$$

$-(CH_2)_m-$phenyl, $-(CH_2)_m-$phenyl$(R_{13})_p$, $-(CH_2)_m-$furyl, $-(CH_2)_m-$thienyl, $-(CH_2)_m-$pyridyl, a 1- or 2-naphthyl or the formula $-(CH_2)_m-$naphthyl, a substituted 1- or 2-naphthyl of the formula $-(CH_2)_m-$naphthyl$(R_{14})_p$, $-(CH_2)_m-$cycloalkyl, $$-O-\overset{O}{\underset{||}{C}}-N\overset{R_{15}}{\underset{R_{15}}{\diagdown}}, -O-\text{lower alkyl}, -O-(CH_2)_m-\text{phenyl},$$

$-O-(CH_2)_m-$phenyl$(R_{13})_p$, a 1- or 2-naphthyloxy of the formula

-continued

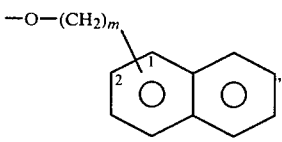

a substituted 1- or 2-naphthyloxy of the formula

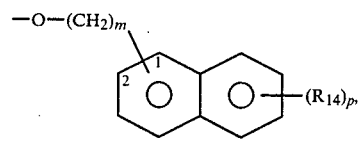

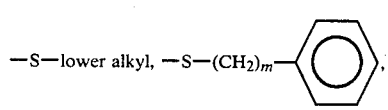

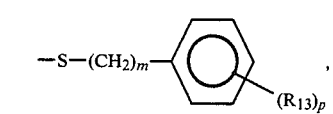

a 1- or 2-naphthylthio of the formula

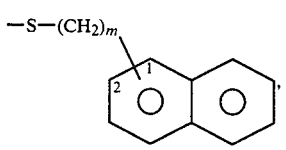

or a substituted 1- or 2-naphthylthio of the formula

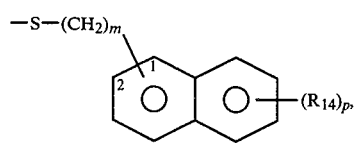

$R_8$ is halogen, 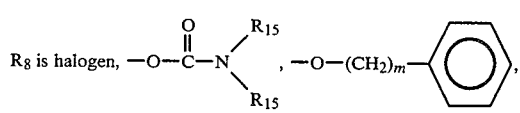

—O—lower alkyl, a 1- or 2-naphthyloxy of the formula

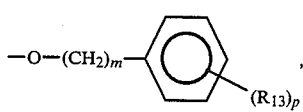

a substituted 1- or 2-naphthyloxy of the formula

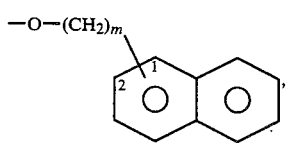

-continued

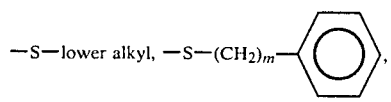

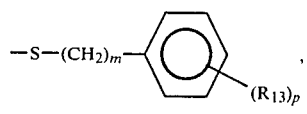

a 1- or 2-naphthylthio of the formula

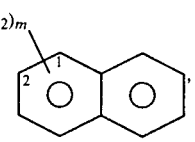

or a substituted 1- or 2-naphthylthio of the formula

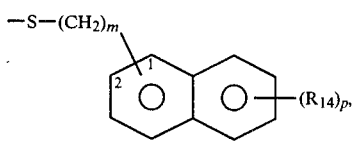

$R_9$ is keto, 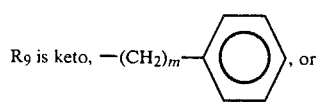, or

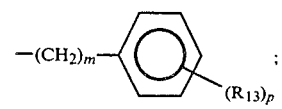;

$R_{10}$ is halogen or —Y—$R_{16}$;
$R_{13}$ is lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl;
$R_{14}$ is lower alkyl of 1 to 4 carbons, lower alkoxy of 1 to 4 carbons, lower alkylthio of 1 to 4 carbons, chloro, bromo, fluoro, trifluoromethyl or hydroxy;
m is zero, one, two, three, or four;
p is one, two or three provided that p is more than one only if $R_{13}$ or $R_{14}$ is methyl, methoxy, chloro, or fluoro;
$R_{15}$ is hydrogen or lower alkyl of 1 to 4 carbons;
Y is oxygen or sulfur;
$R_{16}$ is lower alkyl of 1 to 4 carbons,

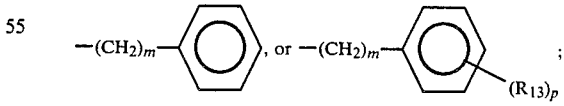;

$R_{19}$ is lower alkyl, benzyl or phenethyl;
$R_{20}$ is hydrogen, lower alkyl, benzyl or phenethyl;
$R_2$ is

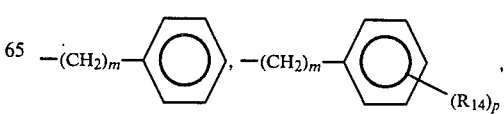

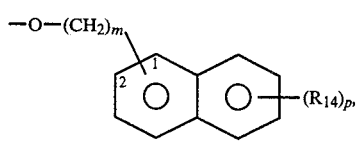

-continued

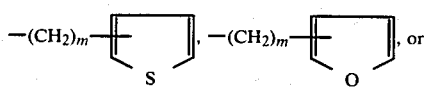

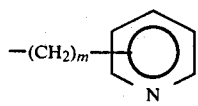

$R_3$ is hydrogen, lower alkyl,

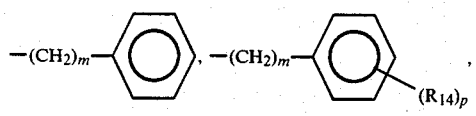

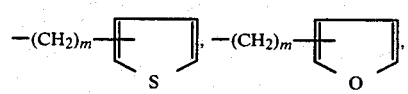

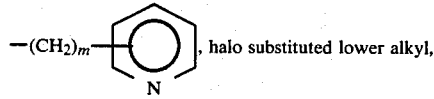, halo substituted lower alkyl,

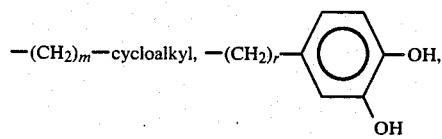

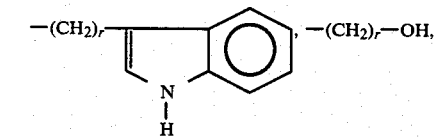

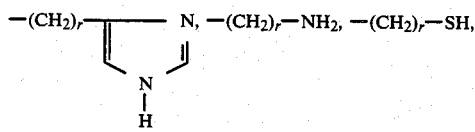

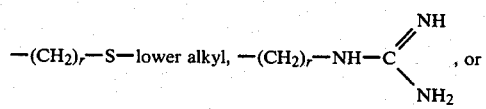

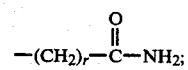

r is an integer from 1 to 4;
$R_6$ is hydrogen, lower alkyl, benzyl, benzhydryl,

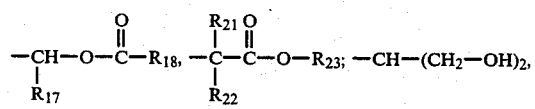

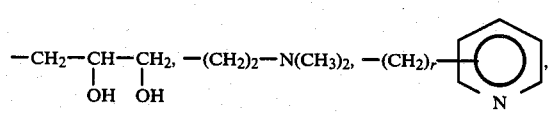

-continued
or pharmaceutically acceptable salt ion;

$R_{17}$ is hydrogen, lower alkyl, cycloalkyl, or phenyl;
$R_{18}$ is hydrogen, lower alkyl, lower alkoxy or phenyl;
$R_{21}$ and $R_{22}$ are independently selected from hydrogen and lower alkyl; and
$R_{23}$ is lower alkyl.

2. A compound of claim 1 wherein:
X is

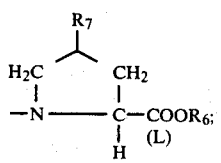

$R_6$ is hydrogen or an alkali metal salt ion;
$R_7$ is hydrogen, cyclohexyl, lower alkoxy of 1 to 4 carbons,

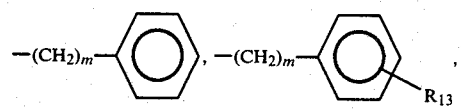

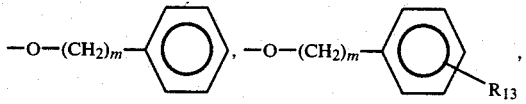

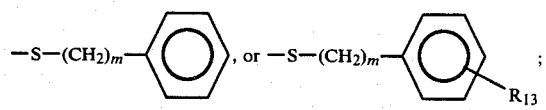

m is zero, one or two; and
$R_{13}$ is methyl, methoxy, methylthio, chloro, bromo, fluoro, or hydroxy.

3. A compound of claim 2 wherein
$R_2$ is

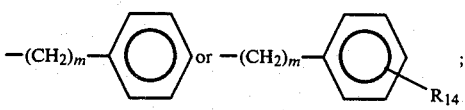

$R_3$ is straight or branched chain lower alkyl of 1 to 4 carbons,

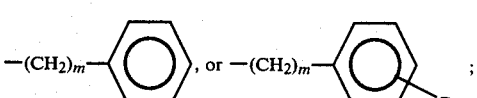

m is zero, one, or two; and
$R_{14}$ is methyl, methoxy, methylthio, Cl, Br, F, or hydroxy.

4. A compound of claim 3 wherein:
Z is sulfur.

5. A compound of claim 3 wherein:
Z is oxygen.

6. A compound of claim 5 wherein:

X is 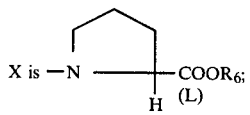

$R_6$ is hydrogen or an alkali metal salt ion;
$R_2$ is phenyl; and
$R_3$ is phenylmethyl.

7. The compound of claim 6, 1-[[[(S)-3-(benzoylamino)-2-oxo-4-phenylbutyl]oxy]carbonyl]-L-proline.

8. A pharmaceutical composition useful for treating hypertension comprising a pharmaceutically acceptable carrier and a hypotensively effective amount of a compound of the formula

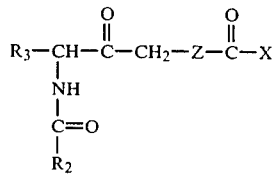

wherein Z, X, $R_2$ and $R_3$ are as defined in claim 1.

9. The method of treating hypertension in a mammalian host which comprises administering a hypotensively effective amount of the composition of claim 8.

* * * * *